United States Patent [19]
Falkowski et al.

[11] Patent Number: 6,121,012
[45] Date of Patent: Sep. 19, 2000

[54] SYSTEM FOR ENSURING DISTRIBUTION OF SPORES ON A SPORE CARRIER

[75] Inventors: Jerry Falkowski, Cary; Mizanu Kebede; Edna I. Hu, both of Durham, all of N.C.

[73] Assignee: Steris Corporation, Mentor, Ohio

[21] Appl. No.: 09/238,870

[22] Filed: Jan. 27, 1999

[51] Int. Cl.$^7$ .............................. C12Q 1/06; C12Q 1/04; C12Q 1/22

[52] U.S. Cl. .................. 435/39; 435/34; 435/4; 435/832; 435/839; 435/31; 435/283.1; 422/50; 422/55

[58] Field of Search .................................. 435/39, 34, 4, 435/832, 839, 31, 283.1; 422/50, 55

[56] References Cited

U.S. PATENT DOCUMENTS

| | | | |
|---|---|---|---|
| 3,346,464 | 10/1967 | Ernst et al. | 435/31 |
| 4,291,122 | 9/1981 | Orelski | 435/31 |
| 4,732,850 | 3/1988 | Brown et al. | 435/39 |
| 4,828,797 | 5/1989 | Zwarun et al. | 435/39 |

OTHER PUBLICATIONS

Abou–Zeid et al, "Indian J. Pharm"., vol. 31(3), p 72–75, (Abstract), 1969.

Tsuda et al, "Chemotherapy", vol. 41(6), p 641–648, (Abstract), 1993.

21 CFR §70—Food and Drugs—Color Additive (1998) Month not available.

*Primary Examiner*—Louise N. Leary
*Attorney, Agent, or Firm*—Fay, Sharpe, Fagan, Minnich & McKee, LLP

[57] ABSTRACT

A suspension of microorganisms includes a detectable indicator material, such as a food coloring, for ensuring that a biological indicator receives a preselected population of the microorganisms. A microorganism delivery system delivers the suspension with the indicator material from a tank (10) to a plurality of needles (18) where it is delivered to a carrier material (22), such as filter, chromatography, or blotter paper, or glass fiber passing beneath the needles or micropipetted onto non-absorptive or non-penetrable carriers, such as plastic polymers or stainless steel coupons. In the event of a malfunction in the system, such as a blockage in one of the needles or intermittent delivery of the microorganism suspension, the absence of color on the impregnated carrier material indicates the absence of microorganisms. The impregnated or otherwise treated carrier material may be evaluated visually or using an automated detector system (32) which signals an alarm in the event that absences in the color or other indicator material are detected.

27 Claims, 1 Drawing Sheet

SYSTEM FOR ENSURING DISTRIBUTION OF SPORES ON A SPORE CARRIER

BACKGROUND OF THE INVENTION

The present invention relates to the sterility assurance arts. It finds particular application in connection with the distribution of microbial spores onto a spore carrier, and will be described with particular reference thereto.

Currently, the instrument of choice for monitoring the effectiveness of a sterilization process is the biological indicator. A typical biological indicator contains a calibrated population of microorganisms having a high resistance to the sterilization process under investigation. After exposure to the sterilization process, the biological indicators are incubated in a culture medium to encourage growth of any remaining viable microorganisms. Self-contained biological indicators contain the culture medium within the indicator, typically in a frangible vial. Spore strip biological indicators are combined with a separate container of culture medium after the monitored sterilization process. Subsequent microbial growth is an indication that the sterilization process was ineffective.

Bacterial spores are favored for biological indicator microorganisms because they are typical of the worst case microbes that are targeted in the sterilization procedure. The selected spores are highly resistant to the physical and chemical agents utilized in the sterilization process. The biological stability of the spores permits the manufacture of a product that exhibits a long shelf life relative to one comprising vegetative cells. The choice of bacteria is dependent on the sterilization to be evaluated. For example, *Bacillus stearothermophilus* spores are used to monitor moist heat sterilization and hydrogen peroxide sterilization because of their high resistance to these processes. Similarly, *Bacillus subtilis* spores are employed to monitor ethylene oxide sterilization, dry heat sterilization, and sterilization systems utilizing peroxy compounds in the plasma state. Because the type of microorganisms in the biological indicator are not readily identifiable by the user, the culture medium of self-contained biological indicators is sometimes color-coded according to the type of sterilization process to be evaluated.

The microorganisms are generally supported on a carrier, such as a spore strip or disk. The carrier is formed from a material which is resistant to the sterilization process and does not contain additives which may influence the sterility assessment. Materials, such as filter paper, chromatography paper, blotter paper, glass fibers, polymer plastics, and stainless steel articles are among those most often used for the carrier.

To distribute the microorganisms on the carrier, a suspension of microorganisms in water is conventionally pumped to a needle which is suspended over a web of the paper or other carrier material. The paper is moved under the needle at a constant rate, causing a trail of the suspension to form on the paper as it passes beneath the needle. Alternatively, the suspension is manually transferred by use of a micropipette to the carrier. The web of impregnated paper is then cut to the appropriate size for inserting into the indicator, typically as strips or disks.

It is important that each of the spore strips or disks contains a calibrated population of the microorganisms. The rate of delivery of the suspension and the rate of transport of the paper are adjusted so that the web receives an even distribution of a selected concentration of the microorganisms. However, occasional malfunctioning of the delivery system can result in uneven distribution of the microorganisms. For example, the needle delivering the microorganism suspension sometimes becomes blocked and the suspension is not delivered to the paper web. Additionally, the pumps used to deliver the microorganism suspension to the needles are generally peristaltic pumps which deliver the suspension as a series of short pulses. This can cause the suspension to be delivered from the needle intermittently, resulting in incomplete coverage of the web. Clearly, a spore strip which is free, or relatively free of microorganisms will be unable to detect an unsatisfactory sterilization process. When nonabsorptive or hydrophobic carriers are inoculated, it is important to be able to tell on which side of the carrier the spores were deposited, for reproducible packaging and subsequent exposure. This recognition is often extremely important for the arrangement of inoculated non-penetrable carriers otherwise the access of a sterilization agent may be hindered.

At present, the method used to evaluate coverage of the paper web is visual observation. Because the microorganism dispersion is generally milky white or clear in color and the blotter paper is also white, it is difficult to determine whether the paper web has been impregnated. Accordingly, an observer constantly monitors the impregnation process to reject regions which are not wetted by the suspension. This method tends to result in a unreliable evaluation of the coverage of the paper web. An observer may fail to spot an unsatisfactory region on the quickly passing paper web. The observer can also monitor the supply of suspension to be sure it is dropping. However, with multi-nozzle systems the suspension still drops when one of the nozzles is clogged.

Additionally, the paper web is not cut to size until after it is dry. Disks for self-contained indicators span a very short length of the paper, typically about 5 mm. At this stage, there is no means of readily checking whether the selected portions of the paper web are coated with microorganisms. As a result, the selected portions may not contain a calibrated microorganism population.

The present invention provides a new and improved indication system for ensuring that a microorganism carrier is impregnated with a population of microorganisms, which overcomes the above-referenced problems and others.

SUMMARY OF THE INVENTION

In accordance with one aspect of the present invention, an apparatus for delivering a population of microorganisms to a carrier material is provided. The system includes a delivery system which supplies a suspension to a carrier. The suspension includes both the microorganisms and a detectable indicator material. The system further includes a detector which evaluates the carrier for the indicator material and provides a signal indicative of the presence or absence of the indicator material on the carrier.

In accordance with another aspect of the present invention, a method for ensuring that a biological indicator receives a population of microorganisms is provided. The method includes mixing a dye with a suspension of microorganisms and distributing the suspension and the dye on a carrier. The method further includes examining the carrier for the presence of the dye.

In accordance with yet another aspect of the present invention, a biological indicator composition is provided. The composition includes a liquid and a detectable indicator material. Microorganisms are suspended in the liquid. The indicator material is one which is detectable irrespective of a viability of the microorganisms without influencing the viability of the microorganisms.

One advantage of the present invention is that it ensures that the spore strip, dot, or other carrier article has been impregnated with a population of microorganisms.

Another advantage of the present invention is that it provides a means of identifying the nature of the microorganisms, or the sterilization process in which the microorganisms are to be used.

Yet another advantage of the present invention is that it does not require verification testing for FDA approval.

Still further advantages of the present invention will become apparent to those of ordinary skill in the art upon reading and understanding the following detailed description of the preferred embodiment.

BRIEF DESCRIPTION OF THE DRAWINGS

The invention may take form in various components and arrangement of components and in various steps and arrangements of steps. The drawings are only for purposes of illustrating a preferred embodiment and are not to be construed as limiting the invention.

The FIGURE is a schematic view of a microorganism distribution system according to the present invention.

DETAILED DESCRIPTION OF THE PREFERRED EMBODIMENTS

Figure 1:
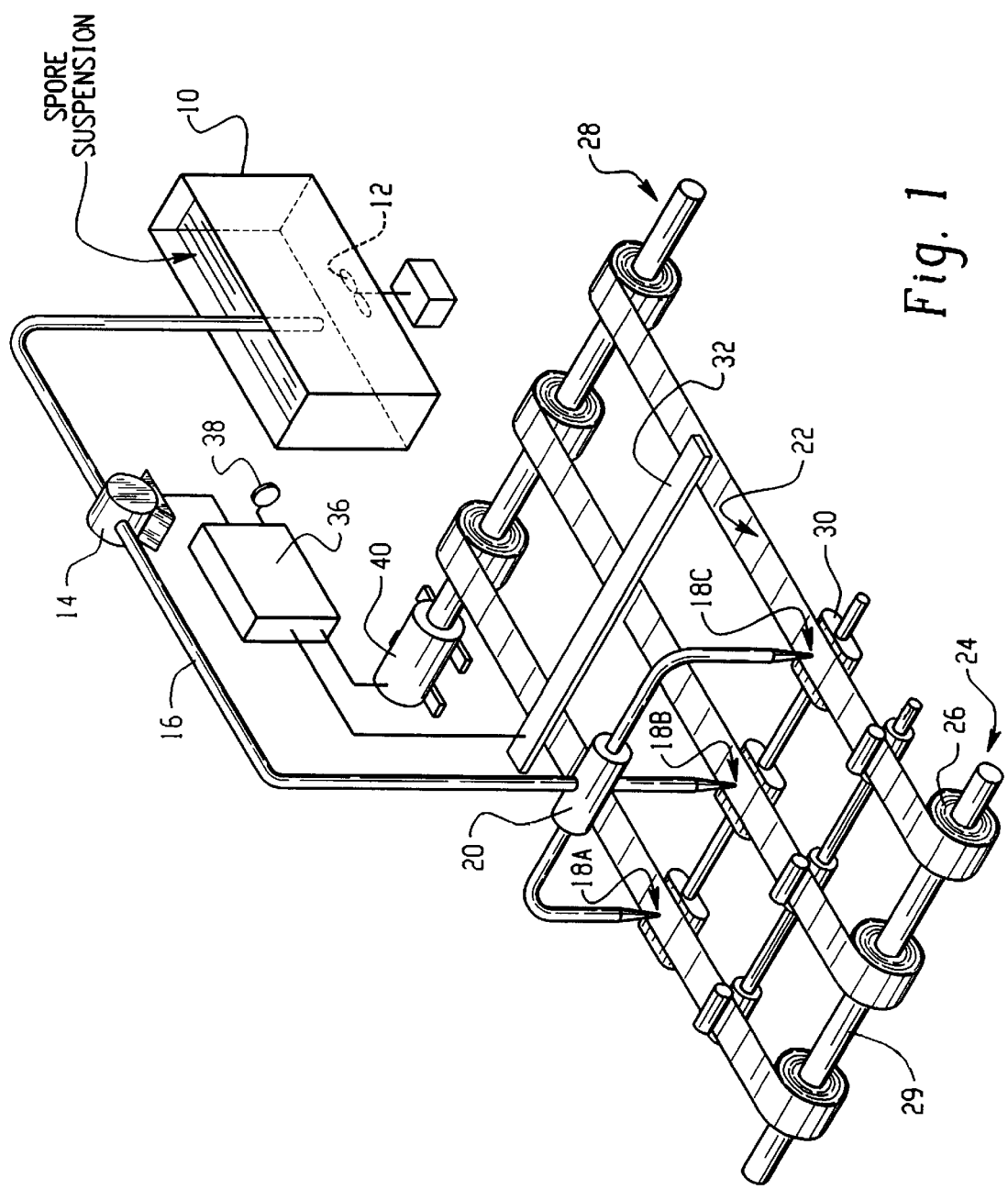

A system for ensuring that a biological indicator receives a calibrated population of microorganisms includes combining an detectable indicator material with a suspension of the microorganisms. The suspension is delivered to a carrier. Subsequent inspection of the carrier allows portions of the carrier which are free of the indicator material, or poorly covered with the indicator material, to be identified and rejected. A portion containing the indicator material, and hence the microorganisms, is used for the biological indicator.

With reference to the FIGURE, a microorganism distribution system includes a reservoir, such as a tank 10, which contains a suspension of test microorganisms, such as bacterial spores, dispersed in a menstrum, such as water. If water is utilized, it is preferably purified and free of additives which may influence the viability of the test microorganisms and free of other microorganisms. Optionally, one or more alcohols may be used in place of a portion of the pure water used in the suspension. A magnetic stirrer 12 stirs the suspension to maintain an even distribution of test microorganisms in the suspension. The suspension includes a known concentration of the test microorganisms. A concentration of around $10^{10}$ viable test microorganisms per liter of suspension is preferred.

The test microorganism is one which has a high resistance to a sterilization process to be evaluated. The choice of microorganism depends on the type of sterilization process to be assessed. While bacterial spores are preferred test microorganisms, because they generally have a high resistance to many sterilization processes, other microorganisms, including yeasts, fungi, and bacteria in the vegetative state, may also be used in place of the spores. Preferred spores include *Bacillus pumilus, Bacillus coagulanis, Clostridium sporegenes, Bacillus subtilis, Bacillus stearothermophilus,* and *Aspergillus niger*, depending on the sterilization system to be evaluated. The test microorganism may be a single specie or a combination of species.

A small amount of a detectable indicator material, such as a visually or spectroscopically detectable dye, is added to the suspension of microorganisms. The dye is preferably one which does not influence the viability of the microorganism, such as a food coloring prepared according to FDA approved specifications, or other cellular, non-toxic dye. Food colorings are particularly preferred dyes because they have been previously certified not to have a biocidal effect, and thus will not interfere with the microorganisms. The food coloring tints the suspension to a preselected color which is readily visible against a white background material. Alternatively, other indicator materials which are readily detectable by a detection instrument, or other means, and which do not interfere with the viability of the microorganisms, are also contemplated.

For ease of reference the invention will be described with reference to a food coloring, or similar visible dye, although it should be understood that other indicator materials are alternatively used.

Preferably, the color of the dye is selected according to the microorganism in the suspension, or according to the sterilization process in which it is to be used. For example, a red food coloring is used for coloring a suspension containing *Bacillus stearothermophilus*, a blue color for a biological indicator containing *Bacillus subtilis*, and a green coloring is used for *Bacillus pumilus*.

A pump, such as a peristaltic pump 14, pumps the suspension tinted with the food coloring at a selected rate along a fluid line 16. The fluid line 16 connects the tank 10 with a plurality of needles 18. In the illustrated embodiment, three needles 18A, 18B, and 18C are used. These are connected with the fluid line 16 via a manifold 20 or other distribution system which ensures an equal distribution of the suspension to each of the needles. The pump is adjustable for varying the rate of delivery of the suspension to the needles.

A carrier material 22, such as a web of filter or blotter paper is supplied from a supply reel assembly 24. The paper is wound onto the reel to form a spool 26 with a starting diameter of about 40 cm. In the illustrated embodiment, three spools are carried on a single shaft 29. The paper webs are delivered from the supply reel assembly 24 to a take-up reel assembly 28. Each of the paper webs passes beneath the corresponding needle 18. A friction drive 30, preferably mounted beneath each of the webs, moves the web at a selected speed in the direction of the take-up reel assembly 28. The impregnated web 22 forms a spool on the take up reel assembly 28.

The tinted suspension flows from the needles 18 onto the paper web 22 passing beneath. A trail of tinted microorganism-impregnated paper is thus formed along the central portion of each web. The trail preferably has a width of approximately 4 mm wide, or greater. The water in the impregnated web evaporates, leaving a region of the paper which is impregnated with the test microorganisms and tinted with the food coloring. Optionally, driers (not shown) are used to accelerate the evaporation.

The presence of the food coloring, or other indicator material, in the paper web allows the paper to be evaluated for the presence of microorganisms at any point during processing of the web. Areas of the web which are free of food coloring are highlighted as containing no microorganisms and are rejected.

The pump 14 and the friction drive 30 are preferably adjusted to provide a desired concentration of microorganisms on the web. A preferred rate of delivery is one which provides a 5 mm diameter disc of the web cut from the impregnated region with about 0.1 ml of the suspension, or a population of $10^6$ microorganisms.

Optionally, a detector 32 is positioned above the microorganism-impregnated web 22 as it passes between the needles and the take-up roller 28. The detector detects for discontinuities in the impregnated region of the web by sensing the color of the impregnated region, or some other detectable property of the indicator material. The detector may be a human observer, who visually scans the passing impregnated web, a photo-optimetric instrument, such as a spectrophotometer, the viabilnstruments which do not influence the viability of the microorganisms during the detection process. The detector is preferably capable of detecting discontinuities in the tinted trail of impregnated paper and regions which are otherwise poorly impregnated.

If a discontinuity in the color is detected, the detector signals a controller 36. For example, the needle 18B of the FIGURE is delivering an interrupted trail of the suspension to the web. The detector recognizes that the trail is not satisfactory and signals the controller.

Where the detector is a spectrophotometer, the spectrophotometer shines a beam of light onto the passing web which is aimed at the region which should be tinted with the dye. The detector receives light reflected from the web and compares the intensity of one or more spectral bands of the received light with the intensity of the same spectral bands for a calibration sample known to be impregnated with the dye. If the measured intensity is below a threshold level, the detector signals the controller 36.

In one embodiment, the controller operates an alarm 38 to provide a visible or audible signal to indicate to an operator that the system has malfunctioned. In another embodiment, the controller 36 controls the coordinated operation of the pump 14 and the friction drive 30 to ensure the prescribed microbe distribution. In response to the detector 32 detecting a malfunction, the controller stops the operation of the system, including halting the pump 14, the friction drive 30, and a take up reel drive 40 until the malfunction can be corrected by an operator.

Optionally, the detector 32 detects a level of tint or other indicator material on the impregnated region of the web which varies with the amount of suspension delivered per unit area of the web. The detector compares the detected level of tint with a preselected set range, corresponding to the tolerance limits for the desired concentration of the microorganisms on the web. The detector determines when the level of tint is outside the preselected range. If the level of tint is outside the preselected range, either above or below the range, the detector signals the controller.

In one embodiment, the controller adjusts the rate of delivery of the suspension to the web in accordance with the detected tint level. This may be done by signaling the friction drive 30 to adjust the rate of transport of the web 22 or signaling the pump 14 to adjust the flow rate of the microorganism suspension in the fluid line 16.

Alternatively, the controller signals an alarm to indicate that the concentration of microorganisms is outside the preselected range. The operator then makes adjustments to the delivery rate or transport rate. In this way, the concentration of microorganisms on the web may be maintained within the preselected range.

The microorganism impregnated paper web is then cut into sections, such as strips or discs, which are inserted into biological indicators. The strips or disks are further checked at this stage for the tint of the food coloring, or other indicator material, to ensure that each biological indicator receives a population of microorganisms. Strips are preferred for spore strip indicators. To form the spore strip indicator, the strip is preferably surrounded by a sheet of a material which provides a challenge to the penetration of sterilants, such as a glassine material, although the strip may also be used without such a sheet. Disks are preferred for self-contained biological indicators. A disc is inserted into a vial which also contains an ample of nutrient media.

The user of the biological indicator is also able to confirm the presence of microorganisms by a quick inspection of the spore strip or disk. When the microorganisms have been color coded, this check also ensures that the correct species for the particular sterilization process are used.

The application of the suspension of microorganisms and indicator material to a carrier has been described with reference to an automated application system, which is a preferred method for achieving a uniform distribution of microorganisms. However, it should be readily appreciated that a variety of other methods for applying the suspension to the carrier may alternatively be employed. For example, the suspension may be manually applied to the carrier, or sprayed from jets onto a sheet of the carrier.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An apparatus for delivering a population of microorganisms to a carrier material, the system comprising:

a delivery system which supplies a suspension to a carrier, the suspension including both the microorganisms and a detectable indicator material; and, a detector which evaluates the carrier for the indicator material and provides a signal indicative of the presence or absence of the indicator material on the carrier.

2. The apparatus of claim 1, wherein the delivery system includes:

a reservoir which contains the suspension;

at least one needle;

a fluid flow line for connected between the reservoir and the at least one needle;

a pump for transporting the suspension along the fluid flow line to the least one needle; and, a transport system for passing the carrier beneath the at least one needle.

3. The apparatus of claim 2, wherein the pump is a peristaltic or continuous pump.

4. The apparatus of claim 2 wherein the microorganisms in the suspension are at a concentration of around $10^{10}$ microorganisms/liter.

5. The apparatus of claim 1, wherein the indicator material includes a dye and the detector includes a photo-optimetric instrument.

6. The apparatus of claim 1, wherein the indicator material is visually detectable and the detector visually observes the carrier material.

7. A method for ensuring that a biological indicator receives a population of microorganisms prior to subjecting the biological indicator to a process intended to kill the received microorganisms, the method comprising the steps of:

prior to a sterilization process, mixing a dye with a suspension of microorganisms;

distributing the suspension and dye mixture on a carrier; and, examining the carrier for the presence of the dye as an indication of the distribution of microorganisms on the carrier.

8. The method of claim 7, wherein the dye consists of food coloring.

9. The method of claim 8, wherein the step of examining the carrier includes:

analyzing the carrier for the presence of the dye by a method selected from the group consisting of visual detection, spectroscopic analysis, photo-optimetric analysis, and combinations thereof.

10. The method of claim 7, further including, after the step of examining the carrier for the dye:

sectioning portions of the carrier in which the dye is present into sections; and, forming a biological indicator with each of the sections.

11. A method for ensuring that a biological indicator receives a population of microorganisms, the method comprising the steps of:

mixing a dye with a suspension of microorganisms, the dye being selected according to a species of the microorganism;

distributing the suspension and dye mixture on a carrier; and examining the carrier for the presence of the dye, the dye indicating both the species of microorganism present on the carrier and the distribution of the microorganisms on the carrier.

12. The method of claim 11, wherein the dye is red and the microorganisms are *Bacillus stearothermophilus* spores.

13. The method of claim 11, wherein the dye is green and the microorganisms are *Bacillus pumilus* spores.

14. The method of claim 11, wherein the dye is blue, and the microorganisms are *Bacillus subtilis* spores.

15. The method of claim 7, wherein the dye is one which does not influence the viability of microorganism.

16. A biological indicator composition for making biological indicator products for being subject to a sterilization process and after the sterilization process being evaluated for the presence of viable microorganism, the composition comprising:

a liquid;

a standardized concentration of viable microorganisms suspended in the liquid; and, a detectable indicator material dispersed in the liquid, the indicator material being one which is detectable irrespective of a viability of the microorganisms without influencing the viability of the microorganisms whereby the detectable material provides an indication that viable organisms entered the sterilization process.

17. The composition of claim 16, wherein the indicator material includes a food coloring.

18. The composition of claim 16, wherein the indicator material includes a dye whose color is selected according to the microorganism and the suspension.

19. The composition of claim 18, wherein the microorganism is *Bacillus stearothermophilus* and the dye is a red food coloring.

20. The composition of claim 18, wherein the microorganism is *Bacillus pumilus* and the dye is a green food coloring.

21. The composition of claim 18, wherein the microorganism is *Bacillus subtilis* and the dye is a blue food coloring.

22. The composition of claim 16, wherein the liquid is selected from the group consisting of water, alcohol, and mixtures thereof.

23. A method of making a biological indicator comprising:

applying the composition of claim 16 to a carrier; and, drying the carrier.

24. A biological indicatior which provides a precise indication that it includes microorganisms, the biological indicator comprising:

a carrier which has been treated with a composition and dried, the composition including:

a liquid, microorganisms suspended in the liquid, and a detectable material, the detectable material being one which is detectable without influencing the viability of the microorganisms.

25. The biological indicator of claim 24, wherein the detecable meterial includes a food coloring.

26. The biological indicator of claim 24, wherein the detectable material includes a dye whose color is selected according to the microorganism in the suspension.

27. The biological indicator of claim 24, further including:

an ample containing a nutrient medium.

* * * * *